United States Patent
Hibner et al.

(10) Patent No.: US 11,439,773 B2
(45) Date of Patent: Sep. 13, 2022

(54) SYSTEM AND METHODS FOR A NON LINEAR NEEDLE GUIDE

(71) Applicant: Dignity Health, San Francisco, CA (US)

(72) Inventors: Michael Hibner, San Francisco, CA (US); Michael A. Bohl, San Francisco, CA (US); Sarah McBryan, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 238 days.

(21) Appl. No.: 16/771,963

(22) PCT Filed: Dec. 18, 2018

(86) PCT No.: PCT/US2018/066305
§ 371 (c)(1),
(2) Date: Jun. 11, 2020

(87) PCT Pub. No.: WO2019/126219
PCT Pub. Date: Jun. 27, 2019

(65) Prior Publication Data
US 2021/0213211 A1 Jul. 15, 2021

Related U.S. Application Data

(60) Provisional application No. 62/662,280, filed on Apr. 25, 2018, provisional application No. 62/599,813, filed on Dec. 18, 2017.

(51) Int. Cl.
*A61M 5/32* (2006.01)
*A61B 1/00* (2006.01)
*A61M 5/42* (2006.01)

(52) U.S. Cl.
CPC .......... *A61M 5/3287* (2013.01); *A61B 1/0014* (2013.01); *A61M 5/427* (2013.01); *A61M 2205/0266* (2013.01); *A61M 2205/3317* (2013.01); *A61M 2205/36* (2013.01);
(Continued)

(58) Field of Classification Search
CPC ........ A61M 5/3287; A61M 2205/0266; A61M 2207/00; A61B 2017/00867; A61B 17/3403; A61B 2017/00946
See application file for complete search history.

(56) References Cited

U.S. PATENT DOCUMENTS

4,702,735 A * 10/1987 Luther .............. A61M 25/0637
604/161
5,061,244 A * 10/1991 Yurkewych ............. A61M 5/46
604/117
(Continued)

*Primary Examiner* — Bradley J Osinski
(74) *Attorney, Agent, or Firm* — Polsinelli PC (57) ABSTRACT

A medical device is disclosed including a needle guide. The needle guide includes abase, a guide member, and a handle arrangement. The base defines a base channel and the guide member includes a guide member channel in communication with one another and configured for receiving a flexible needle. The guide member includes a non-linear portion and is generally flexible to accommodate passage of a flexible needle through a corresponding portion of the guide member channel. The handle arrangement is configured to accommodate stabilization of the needle guide during deployment.

17 Claims, 5 Drawing Sheets

(52) U.S. Cl.
CPC ... *A61M 2205/582* (2013.01); *A61M 2207/00* (2013.01); *A61M 2210/1475* (2013.01)

(56) References Cited

U.S. PATENT DOCUMENTS

| | | | | |
|---|---|---|---|---|
| 2008/0015540 A1* | 1/2008 | Muni | ............... | A61B 17/3421 604/502 |
| 2012/0259292 A1* | 10/2012 | Koehler | ............ | A61M 25/0097 604/256 |
| 2014/0330074 A1* | 11/2014 | Morriss | ............ | A61B 17/32002 606/86 R |

* cited by examiner

SYSTEM AND METHODS FOR A NON LINEAR NEEDLE GUIDE

FIELD

The present disclosure generally relates to a medical device that provides a guide for needles, and more specifically an apparatus and method for providing a non-linear needle guide which may be used for transvaginal injections or other such injection procedures where application of a linear needle is problematic.

BACKGROUND

Spasm of the pelvic floor muscles is one of the most common reasons for chronic pelvic pain in women. It often coincides with other painful conditions such as endometriosis and many others or it may be resulting from a trauma to the pelvis. Even when the original offending factor is resolved, pelvic pain can continue due to ongoing pelvic floor muscle spasms. These types of spasms are debilitating because they can affect the patient's physical activity, sexual activity, and urination/defecation.

Treatment usually consists of muscle relaxants and pelvic floor physical therapy. In more severe cases, injections of Botulinum toxin A can be applied to the pelvic floor muscles. These injections can be very helpful, with over 70% of reported patients achieving pain relief for approximately three months. Currently, these injections are done using pudendal nerve block needles which consist of a long needle and needle guide. The guide allows the surgeon or other clinician to pass the top of the needle into the vagina, against muscle which is experiencing spasms, and advance the needle into the muscle to inject Botox. One of the shortcomings of this existing needle guide relates to the fact that the guide is straight and rigid. Muscles that can spasm have debilitating effects on the patient, including the obturator internus muscle which is behind the pelvic bone and cannot be accessed with a straight needle guide.

It is with these observations in mind, among others, that various aspects of the present disclosure were conceived and developed.

Corresponding reference characters indicate corresponding elements among the view of the drawings. The headings used in the figures do not limit the scope of the claims.

DETAILED DESCRIPTION

Aspects of the present disclosure relate to a flexible non-linear or curved needled guide for use in guiding a needle for injecting any number of substances or other medications into pelvic floor muscles or other muscle or nerve clusters throughout a body. The guide is flexible and configured to assume one or more non-linear shapes or configurations so as to accommodate the positioning of the needle guide in order to access areas of a body that may be obstructed or difficult to reach, such as nerves or muscles behind the pelvic bone or any other impediment that might be found within a human or animal's body. Moreover, by the nature of the needle guide being flexible to a predetermined degree, at least the curved portion of the needle guide may be temporarily or permanently configured as desired.

In some embodiments, the needle guide includes a base, a guide member, and a handle arrangement. The base defines a base channel and the guide member includes a guide member channel in communication with the base channel and configured for receiving a flexible needle. The guide member includes a non-linear portion and may be flexible to accommodate passage of a flexible needle through a corresponding portion of the guide member channel in a predetermined manner. The handle arrangement is configured to accommodate stabilization of the needle guide during deployment. The needle guide may also be configured with a supplementary component such as a heating coil, imaging device, vibration device, or other component mounted along the guide member. Referring to the drawings, one embodiment of a medical device for a flexible non-linear needle guide is illustrated and generally indicated as 100 in FIGS. 1-6.

Figure 1A:
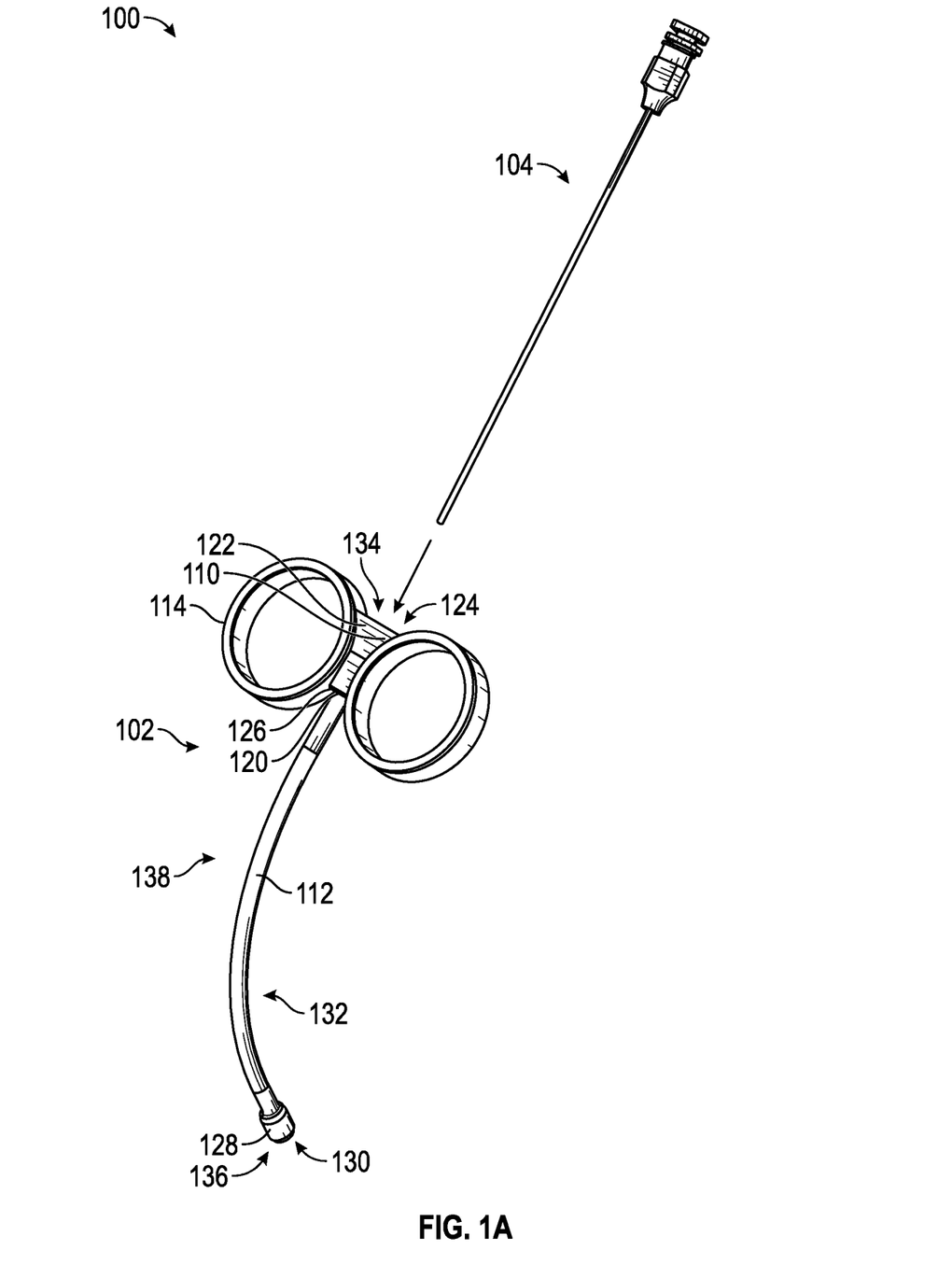
FIG. 1A is a first perspective view of one embodiment of a medical device including a needle guide and a flexible needle.
Figure 1B:
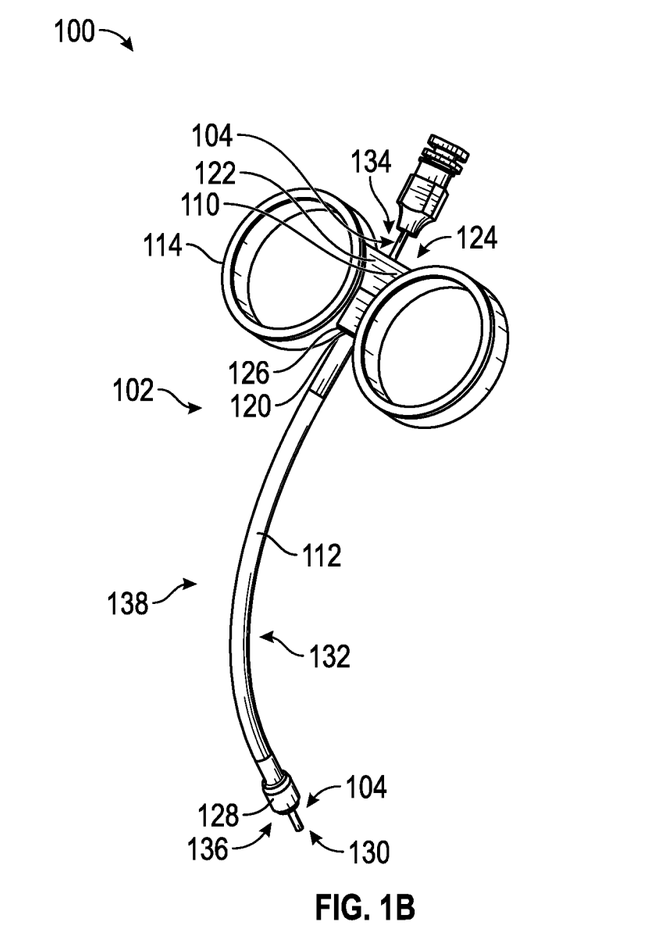
FIG. 1B is a second perspective view of the embodiment of FIG. 1B with the flexible needle received at least partially within the needle guide.

Referring to FIGS. 1A-1B, a medical device 100 is shown for providing non-linear injections or similar medical procedures. The medical device 100 may generally include a needle guide 102 configured for receiving a flexible and/or pliable needle 104. The flexible needle 104 may include any flexible needle or similar device as would be known by one of ordinary skill in the art. In general, the needle guide 102 is configured for receiving at least a portion of the flexible needle 104 as further described herein.

As shown, the needle guide 102 may generally include a base 110, a guide member 112, and a handle arrangement 114. In some embodiments, the base 110 may define a distal end 120 and a proximal end 122, with a base channel 124 extending through the base 110 and defined between the distal end 120 and the proximal end 122 of the base 110. In some embodiments, the base 110 may be generally formed with a rigid configuration to integrate other components of the needle guide 102 as further described herein.

The guide member 112 may generally extend from the distal end 120 of the base 110, and define a proximal end 126 and a distal end 128. A guide member channel 130 extends through the guide member 112 from the proximal end 126 to the distal end 128 and may be in communication with the base channel 124. As further shown, the guide member 112 may define at least one of a non-linear portion 132, which may be curved as shown. The non-linear portion 132 may be formed with dimensions suitable for e.g., navigating the flexible needle 104 along the pelvis for transvaginal injections. One of the shortcomings of conventional needle guides is that such guides are straight and rigid. Muscles that can spasm, having debilitating effects on the patient, include the obturator internus muscle which is behind the pelvic bone and is not easily accessed or may be totally inaccessible with a conventional straight needle guide. The design of the needle guide 102 described herein accommodates access to such injection or surgical sites where muscles are obstructed or difficult to reach, and improves upon related procedures. In other words, the needle guide 102 facilitates the navigation of the flexible needle 104 around any impeding structure or object in order to access and deliver (e.g., inject or "dry needle") any number of substances in any order into a desired location (e.g., a nerve that is behind the pelvic bone), including any other desired location that may be found within the body.

As further shown, the needle guide 102 may include a proximal opening 134 defined by the base channel 124 along the proximal end 122 of the base 110, and a distal opening 136 defined by the guide member channel 130 along the distal end 128 of the guide member 112. A pathway 138 of the needle guide 102 may be collectively defined by the combination of the base channel 124 and the guide member channel 130 between the proximal opening 134 and the distal opening 136. During operation of the medical device 100, the flexible needle 104 may be advanced through the needle guide 102 as shown such that at least a portion of the flexible needle 104 is positioned within and received by the pathway 138. In some embodiments, a portion of the flexible needle 104 may extend from the distal opening 136 outside the pathway 138 as indicated in FIG. 1B. In some embodiments, the proximal opening 134 is configured to receive the flexible needle 104 and has an approximate opening width of about 0.51 centimeters at its widest point. The distal opening 136 is configured to also receive a needle and may be approximately 0.2 centimeters wide. In other embodiments, the proximal opening 134 may define a width of about 0.25 centimeters to about 1.0 centimeters, and the distal opening 136 may define a width of about 0.05 centimeters to about 0.5 centimeters.

Figure 2:
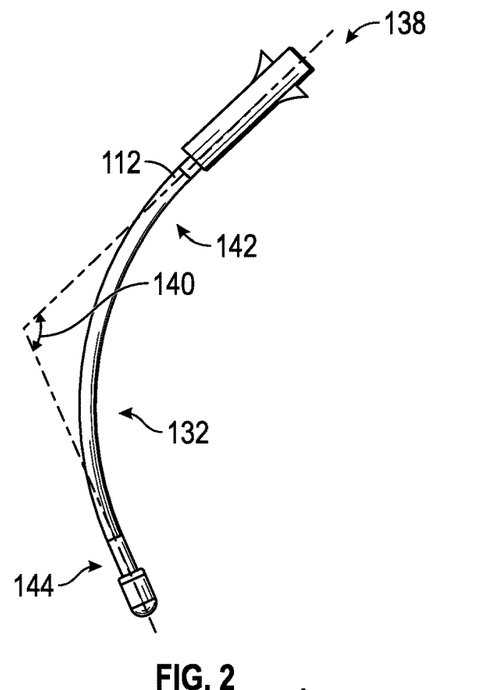
FIG. 2 is a side view of the needle guide of FIGS. 1A-1B.

Referring to FIG. 2, the guide member 112 may be generally hollow (by nature of the pathway 138) and may define a tube or take the form of a tubular shape, but the guide member 112 is not limited in this regard. The guide member 112 and the non-linear portion 132 may be of any length or width. In some embodiments, the guide member 112 may be about 95 centimeters long plus or minus about 50 centimeters and 0.2 centimeters wide plus 2 centimeters or minus 0.1 centimeters.

As shown, the non-linear portion 132 may define an angle 140, defined by an intersection of a first longitudinal axis 142 and a second longitudinal axis 144 of the guide member 112. This angle 140 may include any angle value within 1-360 degrees. As such, the angle 140 of the non-linear portion 132 may comprise an acute angle, an obtuse angle, right angle, or variations thereof. In some embodiments, the non-linear portion 132 may define a general curved portion as shown, such that the angle 140 is generally defined by an arc segment or circular segment. The non-linear portion 132, while indicated as generally being curved, may take other non-linear shapes or configurations, such as arcuate, angled, etc.

Figure 3:
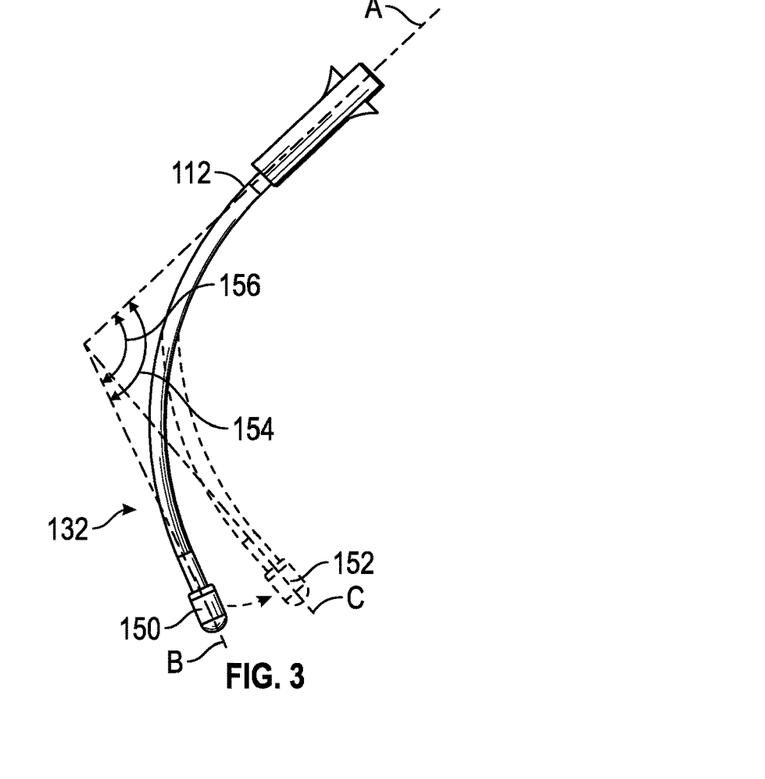
FIG. 3 is a side view of the needle guide of FIGS. 1A-1B illustrating that the needle guide may be temporarily flexed or bent to accommodate different applications.

Referring to FIG. 3, in some embodiments, the non-linear portion 132 and/or the entire guide member 112 may comprise a flexible, malleable, or bendable material allowing the guide member 112 to be bent or modified in a predetermined manner. For example, a user may simply modify aspects of the non-linear portion 132, or may modify the guide member 112 to take on an entirely different configuration altogether. Modification of the non-linear portion 132 and/or the general shape and configuration of the guide member 112 is believed to be an improvement and highly advantageous for accommodating application of the flexible needle 104 of FIG. 1 to a desired location, because modification of the guide member 112 accommodates manipulation of the flexible needle 104 around impediments, such as bones or other muscle groups to inject a nerve grouping or muscle. Conventional needle guide designs lack these non-linear and flexible features described herein. As such, these conventional designs, that are straight and fixed in configuration, are incapable of navigating around obstacles or other impediments to reach a desired placement position to inject nerve and muscles groups.

In the drawing shown, flexibility of the needle guide 102 is illustrated by indicating a change in shape of the guide member 112 from a first configuration 150 to a second configuration 152 which may be effected by bending, temporarily, permanently, or semi-permanently, the distal end 128 of the guide member 112 in the orientation indicated. To demonstrate, a first longitudinal axis A may be defined along a general portion of the guide member 112 as shown. In addition, the first configuration 150 may define a longitudinal axis B as shown, such that a first angle 154 is defined along an intersection between the longitudinal axis A and the longitudinal axis B as indicated. Similarly, the second configuration 152 may define a longitudinal axis C as shown, such that a second angle 156 is defined along an intersection between the longitudinal axis A and the longitudinal axis C as indicated. In other words, as the guide member 112 is modified as shown from the first configuration 150 to the second configuration 152, the general orientation of the non-linear portion 132 relative to the longitudinal axis A is modified resulting in a corresponding change from the angle 154 to the second angle 156. This flexibility provides an improvement with respect to previous devices because this flexibility allows the needle guide 102 to able to navigate around obstacles in an animal's body such as a human; whereas prior devices that have been used for this purpose have been restricted to a straight path to their injection sites.

In some embodiments, portions of the guide member 112 may be rigid and otherwise fixed with respect to form and shape, and other portions, such as the non-linear portion 132, may be flexible, bendable, pliable, and/or malleable to a predetermined degree depending upon the materials used to form the non-linear portion 132 or any such bendable portions. In some embodiments, any portion of the guide member 112 or base 110 may comprise a memory-retaining material such that, for example, the guide member 112 may be oriented in the second configuration 152, but may also be oriented back to the first configuration 150, or vice versa, or other configurations. In some embodiments, the guide member 112 and/or the needle guide 102 may be formed using plastics, metals, steel, aluminum polycarbonate, Delrin, ABS, Nylon, biopolymers, elastomers, fluoropolymers, high-temperature thermoplastics, polyamides, polyesters, polyolefins, or polystyrene/styrenics.

Figure 4:
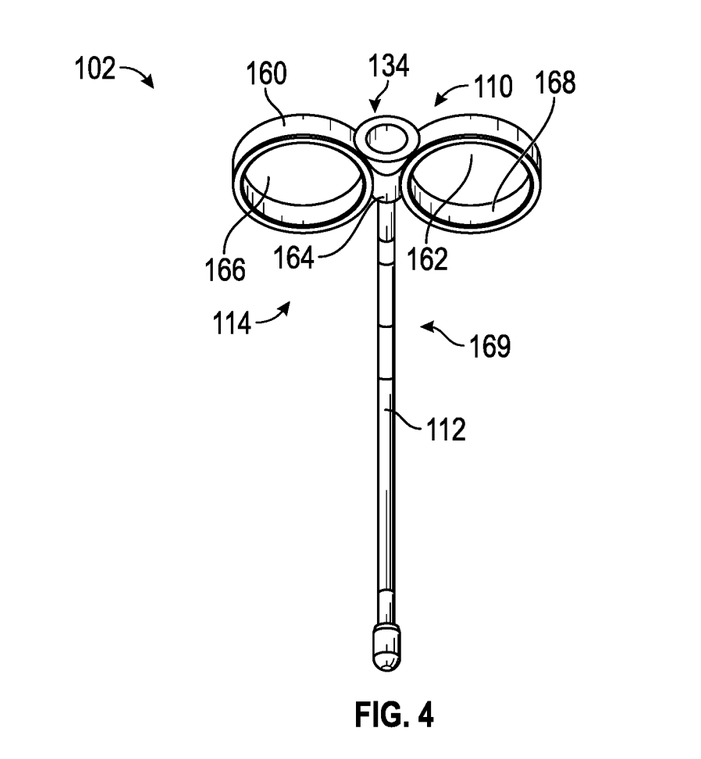
FIG. 4 is a top view of the needle guide of FIGS. 1A-1B.
Figure 5:
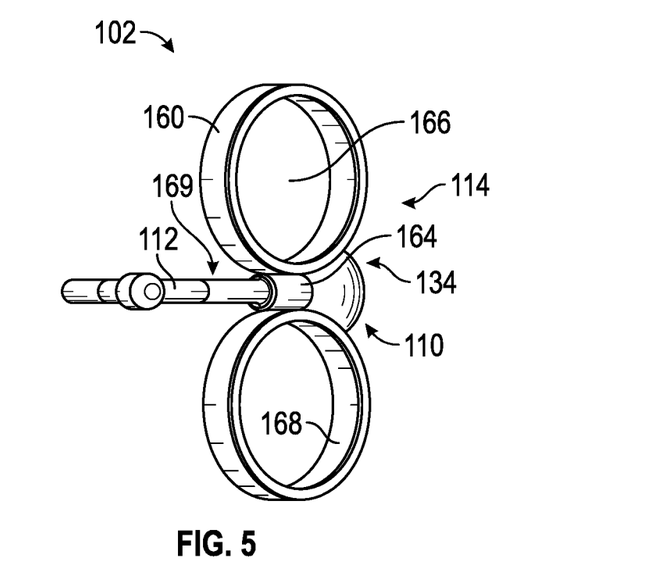
FIG. 5 is a bottom view of the needle guide of FIGS. 1A-1B.

Referring to FIGS. 4-5, the handle arrangement 114 may be positioned along the base 110 as shown, in close proximity to the proximal opening 134 of the needle guide 102. The handle arrangement 114 may define a first ring 160 and a second ring 162 defined along opposite lateral ends of a connecting portion 164 of the handle arrangement 114. The first ring 160 may define an opening 166, and the second opening may define an opening 168. In some embodiments, the opening 166 and the opening 168 may be sized to receive at least one digit of a human finger including a thumb, and in some embodiments may comprise a radius of about 1.55. In some embodiments, the handle arrangement 114 may be generally integral with the base 110.

In some embodiments, the handle arrangement 114 may be configured to slide up or down along a length of the guide member 112. Accordingly, as further indicated, in some embodiments the guide member 112 may define a series of indentations, notches, bumps, or preset fixed locations 169 where the handle arrangement 114 may be positioned relative to the guide member 112.

In some embodiments, additional rings may be defined by the handle arrangement 114, or the handle arrangement 114 may be limited to a sole ring. In addition, it is contemplated that any components of the handle arrangement 114 may be positioned along other locations of the needle guide 102 such as closer to the distal end 128 of the guide member 112 (not shown). In other embodiments, the first ring 160 and the second ring 162 may be partially enclosed rings or may be substituted with magnetic components configured to engage with a corresponding magnetic glove in order to secure the needle guide 102 during use. The first ring 160 and/or the second ring 162 may further be substituted for a bar or other member so long as the handle arrangement 114 accommodates a clinician to grasp the needle guide 102 in some form and stabilize the same during use.

Figure 6:
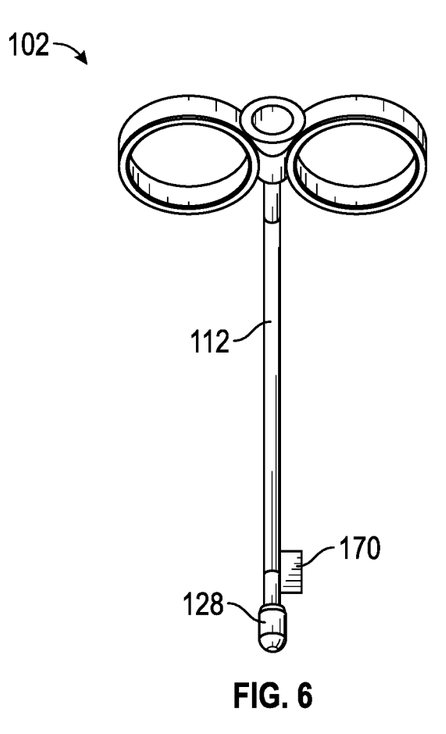
FIG. 6 is a top view of another embodiment of a needle guide which may be incorporated with the medical device of FIGS. 1A-1B that includes at least one supplementary component.

Referring to FIG. 6, the needle guide 102 may include any number of a supplementary component 170. The supplementary component 170 may be mounted or otherwise positioned along the distal end 128 of the guide member 112 as indicated, but the present disclosure is not limited in this regard. The supplementary component 170 may in some embodiments be integrated with one or more components of the needle guide 102 or disposed within the pathway 138.

In some embodiments, the supplementary component 170 may include any number of an electromyography (EMG) device or ultrasound sensors. The supplementary component 170 may further include a vibrating device or heated coil affixed or detachably coupled to the needle guide 102. The supplementary component 170 may further include any sensors to identify nerves or muscles where an injection from the flexible needle 104 would be desired or most effective. Where the supplementary component 170 includes a vibrating device, this vibrating device may be used to disperse or diffuse a substance delivered via the flexible needle 104 (including but not limited to Botox, various poisons, steroids, gels, adhesives, etc.) to a desired location. The supplementary component 170 may further include a heat coil to aid with substance diffusion through the tissue. The supplementary component 170 may further include a stimulator to stimulate nerves or nerve clusters in order to target certain areas.

The supplementary component 170 may further include a camera or endoscope in order to aid with visualizing an area for injection or other treatment using the needle guide 102. In this manner the camera or endoscope need not be constrained by the visible spectrum and may be configured to observe or record an area of use in any range of the spectrum such as infrared, ultraviolet, and the like. In addition, the supplementary component 170 may include or be used in combination with image guidance technologies in order to guide the needle guide 102 and the flexible needle 104 to a desired location. In such embodiments it is possible to couple or affix an image guidance array to the needle guide 102. This image guidance array can be used in conjunction with MRI data and a plurality of reference points in order to navigate the needle guide 102 to areas of interest within a body.

The disclosed needle guide 102 may be used to treat muscle and nerve groups by allowing the flexible needle 104 to be guided around any number or type of obstacles. For example, the needle guide 102 could be used in rectal, transoral or pelvic cavities to guide a needle to inject muscles or nerves. Additionally, the needle guide 102 could be used with any cavity in the body; either natural, wound or surgically created. In some embodiments, the needle guide 102 is may be used for brief guidance of the flexible needle 104 to inject a nerve or muscle group. However, in other embodiments the needle guide 102 can be used for greater periods of time for tasks such as for threading a catheter. Prior devices have always been held back or restricted due to inflexibility and/or lack of a curve. The disclosed inventive needle guide 102 overcomes these restrictions by accommodating one or more curved or non-linear configurations suitable for navigating around obstacles within the body cavities of a human or animal.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A medical device, comprising:
   a needle guide, including:
      a base, the base defining a base channel extending through the base, the base further defining a proximal opening of the needle guide along a first end of the base channel,
      a guide member in communication with the base, the guide member defining a guide member channel extending through the guide member and in communication with the base channel, the guide member further including a curved portion and being configurable with a predetermined degree of flexibility, and
      a handle arrangement engaged along the guide member and configured for stabilizing the needle guide along a surgical site wherein the handle arrangement defines:
         a pair of rings extending laterally from a mounting element, the mounting element slidably engaged along the guide member.

2. The medical device of claim 1, wherein the predetermined degree of flexibility of the guide member accommodates a predetermined modification to an angle defined by the curved portion.

3. The medical device of claim 1, further comprising: a needle defining a flexible needle shaft configured for at least partial insertion through the guide member channel of the needle guide.

4. The medical device of claim 1, further comprising:
   a supplementary component positioned along the guide member.

5. The medical device of claim 4, wherein the supplementary component includes at least one sensor positioned along the guide member.

6. The medical device of claim 4, wherein the supplementary component includes an injection component positioned along the guide member and configurable to accommodate diffusion of a substance traversing the guide member.

7. The medical device of claim 4, wherein the supplementary component includes a camera or endoscope to aid with positioning of the needle guide along an injection point or surgical site.

8. The medical device of claim 1, wherein the curved portion defines an arc segment formed along the guide member between opposite linear ends of the guide member.

9. The medical device of claim 1, wherein the guide member is removably attached to the base.

10. The medical device of claim 1, wherein an entire length of the guide member is flexible.

11. The medical device of claim 1, wherein the guide member is at least partially formed with a malleable memory-retaining material.

12. The medical device of claim 1, wherein the handle arrangement is removably attached to a predetermined location along the needle guide.

13. The medical device of claim 1, wherein the handle arrangement defines at least one opening for receiving a digit of a clinician.

14. A medical device, comprising:
a needle guide for receiving a flexible needle, including:
   a base, the base defining a base channel extending through the base, the base further defining a proximal opening of the needle guide along a first end of the base channel,
   a guide member in communication with the base, the guide member defining a guide member channel extending through the guide member and in communication with the base channel, the guide member including a non-linear portion and formed with a predetermined degree of flexibility, and
   a handle arrangement engaged along the guide member and configured for stabilizing the needle guide along a surgical site, wherein the handle arrangement defines a pair of rings extending laterally from a mounting element, the mounting element slidably engaged along the guide member.

15. The medical device of claim 14, wherein the non-linear portion defines an arc segment defined along the guide member between opposite linear ends of the guide member.

16. The medical device of claim 15, wherein the arc segment is configurable to be temporarily modified by nature of the predetermined degree of flex capability of the guide member.

17. The medical device of claim 14, wherein the needle guide is formed using a biocompatible resin.

\* \* \* \* \*